(12) United States Patent
Takeda et al.

(10) Patent No.: US 8,173,838 B2
(45) Date of Patent: May 8, 2012

(54) METHOD FOR PRODUCING AT LEAST ONE OF α, β-UNSATURATED ALDEHYDE AND α, β-UNSATURATED CARBOXYLIC ACID

(75) Inventors: Akio Takeda, Hiroshima (JP); Yuji Fujimori, Hiroshima (JP); Seiichi Kawato, Tokyo (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 435 days.

(21) Appl. No.: 12/443,994

(22) PCT Filed: Oct. 3, 2006

(86) PCT No.: PCT/JP2006/319782
§ 371 (c)(1),
(2), (4) Date: Jun. 3, 2009

(87) PCT Pub. No.: WO2008/041325
PCT Pub. Date: Apr. 10, 2008

(65) Prior Publication Data
US 2010/0094045 A1    Apr. 15, 2010

(51) Int. Cl.
*C07C 51/16* (2006.01)
*C07C 45/00* (2006.01)

(52) U.S. Cl. ........ 562/533; 562/532; 562/545; 562/546; 568/476

(58) Field of Classification Search .......... 562/518, 562/521, 535, 532, 533, 545, 546; 568/476
See application file for complete search history.

(56) References Cited

FOREIGN PATENT DOCUMENTS

| JP | 58-116427 | | 7/1983 |
|---|---|---|---|
| JP | 63-216835 | * | 9/1988 |
| JP | 1 160938 | | 6/1989 |
| JP | 6 321845 | | 11/1994 |
| JP | 2003 261493 | | 9/2003 |
| JP | 2004 130261 | | 4/2004 |
| JP | 2004-141863 | * | 5/2004 |
| JP | 2004 141863 | | 5/2004 |
| JP | 2006 265227 | | 10/2006 |

OTHER PUBLICATIONS

Stuchinskaya, T. et al., "Liquid-Phase Oxidation of Alcohols with Oxygen Catalysed By Modified Palladium (II) Oxide", Catalysis Coummunications, vol. 4, No. 8, pp. 417-422 (2003).
Office Action, in Japanese Patent Application No. 2005-354978, filed Oct. 21, 2011.

* cited by examiner

*Primary Examiner* — Taylor Victor Oh
(74) *Attorney, Agent, or Firm* — Oblon, Spivak, McClelland, Maier & Neustadt, L.L.P.

(57) ABSTRACT

Disclosed is a method for producing at least one of an α,β-unsaturated aldehyde and an α,β-unsaturated carboxylic acid from an alcohol in a liquid phase through a simple process. Namely, at least one of an α,β-unsaturated aldehyde and an α,β-unsaturated carboxylic acid is produced by dehydrating and oxidizing an alcohol in a liquid phase at 110 to 250° C. in the presence of molecular oxygen and a noble metal-containing catalyst. Alternatively, at least one of an α,β-unsaturated aldehyde and an α,β-unsaturated carboxylic acid is produced by dehydrating and oxidizing an alcohol in a liquid phase in the presence of molecular oxygen, a noble metal-containing catalyst, and an acidic substance.

20 Claims, No Drawings

METHOD FOR PRODUCING AT LEAST ONE OF α, β-UNSATURATED ALDEHYDE AND α, β-UNSATURATED CARBOXYLIC ACID

CROSS REFERENCE TO RELATED APPLICATION

This application is a 371 of PCT/JP06/319782, filed on Oct. 3, 2006.

TECHNICAL FIELD

The present invention relates to a method for producing at least one of an α,β-unsaturated aldehyde and an α,β-unsaturated carboxylic acid from an alcohol in a liquid phase.

BACKGROUND ART

For example, there is disclosed a method for producing an α,β-unsaturated carboxylic acid from an olefin or an α,β-unsaturated aldehyde in a liquid phase in the presence of molecular oxygen and a palladium-containing catalyst in Patent Document 1. When the olefin is used as a raw material in this method, an α,β-unsaturated aldehyde is also produced, and hence this method can be applicable as a method for producing at least one of an α, β-unsaturated aldehyde and an α,β-unsaturated carboxylic acid depending on purposes.

Further, there is disclosed a method for producing methacrolein and methacrylic acid from t-butanol in a gas phase in the presence of molecular oxygen and a molybdenum-bismuth-iron based catalyst in Patent Document 2.

Patent Document 1: Japanese Patent Application Laid-Open No. 2004-141,863
Patent Document 2: Japanese Patent Application Laid-Open No. 2004-130,261

DISCLOSURE OF INVENTION

Problem to be Solved by the Invention

According to the method in Patent Document 2, it seems that it is theoretically possible to produce at least one of an α,β-unsaturated aldehyde and an α,β-unsaturated carboxylic acid from not only t-butanol but also other alcohols. However, there are problems such that the size of devices such as reactor to be used in this method is large and the reaction temperature becomes high.

Generally, the size of devices is small in the cases of liquid-phase reactions, however, in the method described in Patent Document 1, an alcohol such as t-butanol does not react, so that it is impossible to produce at least one of an α,β-unsaturated aldehyde and an α,β-unsaturated carboxylic acid by simply applying this method. Consequently, it is necessary to add a step of dehydration reaction for producing an olefin from an alcohol such as t-butanol. The dehydration reaction for producing an olefin from an alcohol is an endothermic reaction, so that energy for heating is necessary at the time of the reaction. While an oxidation reaction for producing at least one of an α,β-unsaturated aldehyde and an α,β-unsaturated carboxylic acid from an olefin is an exothermic reaction, so that heat removal is necessary. Such being the case, it is economically disadvantageous to provide the steps of dehydration reaction and oxidation reaction separately because this causes an increase in reaction steps, and moreover, it is practically difficult to carry out these reactions in one vessel.

Consequently, it is an object of the present invention to provide a method for producing at least one of an α,β-unsaturated aldehyde and an α,β-unsaturated carboxylic acid capable of carrying out a dehydration reaction and an oxidation reaction of an alcohol in a liquid phase in one vessel and in one step.

Means for Solving the Problem

The present invention is a method for producing at least one of an α,β-unsaturated aldehyde and an α,β-unsaturated carboxylic acid from an alcohol, which comprises dehydrating and oxidizing the alcohol in a liquid phase in the presence of molecular oxygen and a noble metal-containing catalyst at a temperature in the range of 110 to 250° C.

Further, the present invention is a method for producing at least one of an α,β-unsaturated aldehyde and an α,β-unsaturated carboxylic acid from an alcohol, which comprises dehydrating and oxidizing the alcohol in a liquid phase in the presence of molecular oxygen, a noble metal-containing catalyst, and an acidic substance.

Effect of the Invention

According to the present invention, at least one of an α,β-unsaturated aldehyde and an α,β-unsaturated carboxylic acid can be produced from an alcohol in a liquid phase through a simple process.

BEST MODE FOR CARRYING OUT THE INVENTION

In the present invention, at least one of an α,β-unsaturated aldehyde and an α,β-unsaturated carboxylic acid is produced by reacting an alcohol in a liquid phase in the presence of molecular oxygen and a noble metal-containing catalyst (hereinafter, also merely referred to as "catalyst").

Hereinafter, a method for producing at least one of an α,β-unsaturated aldehyde and an α,β-unsaturated carboxylic acid by reacting the alcohol will be explained.

As the alcohol which is a raw material, one which gives an olefin that is produced by intramolecular dehydration of the alcohol and has the same carbon skeleton as at least one of an α,β-unsaturated aldehyde and an α,β-unsaturated carboxylic acid (hereinafter, also referred to as "target substance") can be used, and for example, isopropanol, t-butanol, and n-butanol can be mentioned. The present invention is suitable when the alcohol is isopropanol or t-butanol. In that case, the specific target substance is at least one of acrolein and acrylic acid which has the same carbon skeleton as propylene when the raw material is isopropanol, or at least one of methacrolein and methacrylic acid which has the same carbon skeleton as isobutylene when the raw material is t-butanol.

A solvent to be used in the reaction (i.e., reaction solvent) is not particularly limited, and for example, water, ketones, organic acids, organic acid esters, and hydrocarbons can be used. As the ketones, for example, acetone, methyl ethyl ketone, diethyl ketone, methyl isobutyl ketone, di-n-propyl ketone, and diisopropyl ketone can be mentioned. As the organic acids, for example, acetic acid, n-valeric acid, and isovaleric acid can be mentioned. As the organic acid esters, for example, ethyl acetate and methyl propionate can be mentioned. As the hydrocarbons, for example, hexane, cyclohexane, and toluene can be mentioned. In addition, it is also possible to use an alcohol which is the raw material of the reaction as the solvent, and in this case, the alcohol functions as both the solvent and the raw material. Among these solvents, ketones having 3 to 6 carbon atoms, t-butanol, and isopropanol are preferable. These solvents can be used alone or in a combination of two or more kinds.

Further, when at least one compound of alcohols, ketones, and organic acid esters is used, it is preferable to use it as a mixed solvent with water. The quantity of water in the mixed solvent is not particularly limited, however, it is preferably 2% by mass or more based on the mass of the mixed solvent, and more preferably 5% by mass or more, and preferably 70% by mass or less and more preferably 50% by mass or less. The mixed solvent is preferably homogeneous, however, it is possible to use it in an inhomogeneous state.

The present reaction may be carried out by any one process of continuous process and batch process, however, it is preferably carried out by continuous process industrially in consideration of productivity.

When a solvent other than alcohols is used, the quantity of an alcohol which is the raw material in a reaction liquid is preferably 0.5% by mass or more based on the solvent existing in a reactor and more preferably 2% by mass or more.

As a source for molecular oxygen to be used in the liquid-phase oxidation reaction, air is economical, however, pure oxygen or a mixed gas of pure oxygen and air can also be used, and if necessary, a diluted mixed gas in which air or pure oxygen is diluted with nitrogen, carbon dioxide, water vapor, or the like can also be used. The gas such as air is preferably supplied in a pressurized state into a reactor such as autoclave.

The quantity of molecular oxygen is preferably 0.1 mole or more to 1 mole of an alcohol, more preferably 0.3 mole or more, and furthermore preferably 0.5 mole or more, and preferably 30 moles or less, more preferably 25 moles or less, and furthermore preferably 20 moles or less when a solvent other than alcohols is used. When an alcohol is used as a solvent, the quantity of molecular oxygen is preferably 0.005 mole or more to 1 mole of the alcohol and more preferably 0.01 mole or more, and preferably 10 moles or less and more preferably 5 moles or less.

The catalyst is preferably used in a suspended state in the reaction liquid, however, it may be used in a fixed bed. The quantity of the catalyst to be used is preferably 0.1% by mass or more as the catalyst existing in the reactor based on the solution existing in the reactor in which liquid-phase oxidation is carried out, more preferably 0.5% by mass or more, and furthermore preferably 1% by mass or more, and preferably 30% by mass or less, more preferably 20% by mass or less, and furthermore preferably 15% by mass or less.

The reaction temperature and the reaction pressure are properly selected depending on the solvent and the raw material of the reaction to be used. The reaction temperature exerts influence on the rate of reaction and productivity (production quantity per unit time) of the target substance. The reaction temperature is generally preferably 50° C. or above, more preferably 70° C. or above and furthermore preferably 90° C. or above. The reaction temperature is particularly preferably 110° C. or above in consideration of the rate of reaction and productivity of the target substance. And the reaction temperature is preferably 250° C. or below and more preferably 200° C. or below. The reaction pressure is preferably 0 MPa or above (in gauge pressure; hereinafter, all pressures being expressed in gauge pressure) and more preferably 2 MPa or above, and preferably 10 MPa or below and more preferably 7 MPa or below.

The present invention can be carried out in the presence of an acidic substance. The acidic substance mentioned here is a substance having an $H_0$ (Hammett Acidity Function) of not higher than +4.8. The $H_0$ can be measured using Hammett indicators (color indicator). Specifically, methyl red as a Hammett indicator is a substance that shows acidic color.

The effect of addition of the acidic substance is to efficiently promote the change from an alcohol to an olefin by dehydration of alcohol and hence to improve the rate of reaction of the oxidation reaction step. As the acidic substance to be used in the present invention, for example, inorganic acids, heteropoly acids and their salts, and solid acids can be mentioned. As the inorganic acids, for example, sulfuric acid and phosphoric acid can be mentioned. As the heteropoly acids and their salts (hereinafter, also referred to as "heteropoly acids (salts)"), for example, heteropoly acids such as phosphomolybdic acid, phosphotungstic acid, silicomolybdic acid, and silicotungstic acid, and salts of these heteropoly acids can be mentioned. As the solid acids, for example, metal oxides such as silica, alumina, silica-alumina, γ-alumina, zirconia, and titania, various zeolites such as HY type zeolite and mordenite, and strongly acidic ion-exchange resins can be mentioned. Among them, solid acids are preferable and γ-alumina, zirconia, titania, various zeolites, and strongly acidic ion-exchange resins are more preferable when a material of a device, separation, and disposal treatment of a discarded acid are considered. These acidic substances can be used alone or in a combination of two or more kinds. The solid acid can be caused to exist in the reaction system as a carrier of a noble metal-containing catalyst which will be mentioned later. In this case, HY type zeolite, silica, silica-alumina, zirconia, titania, or a strongly acidic ion-exchange resin is preferable as the carrier. In addition, the solid acids may be modified by metal ions.

As a preferable embodiment of the present invention, the reaction temperature is set in the range of from 50 to 250° C. in the presence of the acidic substance. Like this, by causing the acidic substance to exit, it is possible to carry out the reaction even at a relatively low temperature. The reaction temperature in this case is preferably in the range of from 50 to 200° C. and more preferably 70 to 150° C. Further, the reaction temperature is set in the range of from 110 to 250° C. in the absence of the acidic substance. Even under the absence of the acidic substance as mentioned above, the reaction can be advanced if the temperature is not below 110° C. in this case, the reaction temperature is preferably in the range of from 110 to 230° C. and more preferably from 120 to 200° C.

It is preferable to add enough quantity of the acidic substance to the reaction system to be able to produce an olefin enough for the advancement of the oxidation reaction because the effect of addition of the acidic substance is to effectively produce the olefin by dehydrating an alcohol. The concentration of the acidic substance is preferably 0.1% by mass or more based on the reaction solvent, more preferably 0.2% by mass or more, and particularly preferably 0.5% by mass or more, and preferably 50% by mass or less, more preferably 40% by mass or less, and particularly preferably 30% by mass or less.

The catalyst to be used in the present invention is a noble metal-containing catalyst. The noble metals to be contained in the catalyst are palladium, platinum, rhodium, ruthenium, iridium, gold, silver, and osmium, and among them, palladium, platinum, rhodium, ruthenium, iridium, and gold are preferable, and above all, palladium is particularly preferable. The catalyst may contain two or more kinds of noble metals and may contain elements other than noble metals.

The catalyst to be used in the present invention can contain one or more metal components other than noble metals. As the metal components other than noble metals, for example, copper, antimony, tellurium, lead, and bismuth can be mentioned. It is preferable that the content of a noble metal among the metals contained in the catalyst be 50% by mass or more from the viewpoint of realizing a high catalyst activity.

The catalyst may be either a supported catalyst in which a noble is supported on a carrier or an unsupported catalyst in which a carrier is not used, however, the supported catalyst is preferable because separation of the catalyst and the reaction liquid is easy. In the case of the supported catalyst, the loading ratio of the metal components including the noble metal with respect to the carrier is preferably 0.1% by mass or more to the carrier that is before the metal components have been supported, more preferably 0.5% by mass or more, and furthermore preferably 1% by mass or more, and preferably 40% by mass or less, more preferably 30% by mass or less, and furthermore preferably 20% by mass or less.

As the catalyst, for example, one on the market and one produced by reducing a compound containing a noble metal in its oxidation state (hereinafter, also referred to as "a noble metal compound") can be used. When the catalyst on the market is used, it is preferable to use an activated catalyst obtained by bringing the catalyst into contact with a reducing agent.

Hereinafter, a method for producing a catalyst by reducing the noble metal compound will be explained.

The noble metal compound to be used is not particularly limited, however, for example, chlorides, oxides, acetates, nitrates, sulfates, tetraammine complexes, and acetylacetonate complexes of the noble metal are preferable, and chlorides, acetates, and nitrates of the noble metal are more preferable. In the case of producing a catalyst containing one or more metal components other than the noble metal, metal compounds such as salts or oxides of the aforementioned corresponding metal components are jointly used.

Reduction treatment is carried out by bringing the noble metal compound into contact with a reducing agent. The reduction treatment may be carried out either in a liquid phase or in a gas phase and not particularly limited. Hereinafter, the reduction treatment in the liquid phase will be mainly explained.

At first, a solution obtained by dissolving the noble metal compound in a solvent is prepared. The concentration of the noble metal compound in the solution is preferably 0.1% by mass or more, more preferably 0.2% by mass or more, and particularly preferably 0.5% by mass or more, and preferably 20% by mass or less, more preferably 10% by mass or less, and particularly preferably 7% by mass or less.

When a catalyst supported on a carrier is produced, a method in which either the carrier is soaked in this solution or this solution is impregnated into the carrier (referred to as "pore filling"), and then a reducing agent is added to reduce the noble metal compound, a method in which the solvent is evaporated from the carrier subjected to pore filling to prepare a catalyst precursor in which the noble metal salt is dispersed on the carrier, and then reduction using a reducing agent is carried out, or a method in which the catalyst precursor is subjected to heat treatment to cause at least a part of the noble metal salt to change into an oxide of the noble metal, and then reduction using a reducing agent is carried out can be used.

Among these methods, the method of reducing the oxide obtained by heat treatment is preferable. When the heat treatment is carried out, the temperature of the heat treatment is preferably not lower than the thermal decomposition temperature of the noble metal salt, and preferably 800° C. or lower and more preferably 700° C. or lower. The rate of heating to a predetermined temperature of the heat treatment is not particularly limited, however, it is preferably 1° C./minute or more and preferably 10° C./minute or less in order to obtain an excellent dispersion state of the noble metal atom in the final noble metal-containing catalyst. The holding time after reaching the predetermined temperature of the heat treatment is not particularly limited as long as it is enough for decomposing the noble metal salt, however, it is preferably 1 hour or more and preferably 12 hours or less.

The method for loading the metal compounds to be used in the case of producing the catalyst containing one or more metal components other than the noble metal is not particularly limited, however, the same method can be used as in the case of loading the noble metal compound. In addition, the metal compounds can be supported before the noble metal compound is supported or after the noble metal compound is supported or together with the noble metal compound at the same time.

The carrier is not particularly limited as long as it can support the noble metal. For example, activated carbon, carbon black, silica, alumina, silica-alumina, magnesia, calcia, titania, zirconia, and various zeolites can be mentioned. In the present invention, the method of supporting a noble metal salt on a carrier followed by heat treatment of the carrier is adopted as a preferable embodiment as mentioned above, so that it is preferable to use, as the carrier, an inorganic oxide which is hardly combustible or does not easily change in quality. For example, silica, alumina, silica-alumina, magnesia, calcia, titania, zirconia, and various zeolites are preferable. Among them, silica, titania, zirconia, and various zeolites are more preferable. These carriers can be used alone or in a combination of two or more kinds. Further, a carrier functioning as a solid acid can also be used as mentioned above.

A preferable range of specific surface area of the carrier varies depending on a kind of the carrier and cannot be absolutely said, however, in the case of activated carbon, it is preferably 100 m$^2$/g or more and more preferably 300 m$^2$/g or more, and preferably 5,000 m$^2$/g or less and more preferably 4,000 m$^2$/g or less. In the case of zeolite, it is preferably 100 m$^2$/g or more and more preferably 200 m$^2$/g or more, and preferably 4,000 m$^2$/g or less and more preferably 3,000 m$^2$/g or less. As the specific surface area of the carrier becomes smaller, production of a catalyst in which its useful components are supported more on its surface becomes possible, and as the specific surface area of the carrier becomes larger, production of a catalyst in which its useful components are supported more becomes possible.

As the solvent to be used for dissolving the noble metal compound, water is preferable, however, solvents like alcohols such as ethanol, 1-propanol, 2-propanol, n-butanol, and t-butanol; ketones such as acetone, methyl ethyl ketone, methyl isobutyl ketone, and cyclohexanone; organic acids such as acetic acid, n-valeric acid, and isovaleric acid; and hydrocarbons such as heptane, hexane, and cyclohexane can be used alone or in a combination of two or more kinds, depending on solubility of noble metal compound and the dispersibility of a carrier in the case of using the carrier. Further, a mixed solvent of these compounds and water can also be used.

The reducing agent to be used is not particularly limited, and for example, hydrazine, formaldehyde, sodium borohydride, hydrogen, formic acid, a formate salt, ethylene, propylene, 1-butene, 2-butene, isobutylene, 1,3-butadien, 1-heptene, 2-heptene, 1-hexene, 2-hexene, cyclohexene, allyl alcohol, methallyl alcohol, acrolein, and methacrolein can be mentioned. The reducing agent can be used alone or in a combination of two or more kinds. In gas-phase reduction, hydrogen is preferable as the reducing agent. In liquid-phase reduction, hydrazine, formaldehyde, formic acid, and a formate salt are preferable.

As the solvent to be used at the time of liquid-phase reduction, water is preferable, however, solvents like alcohols such as ethanol, 1-propanol, 2-propanol, n-butanol, and t-butanol; ketones such as acetone, methyl ethyl ketone, methyl isobutyl ketone, and cyclohexanone; organic acids such as acetic acid, n-valeric acid, and isovaleric acid; and hydrocarbons such as heptane, hexane, and cyclohexane can be used alone or in a combination of more than one kind, depending on solubility of the reducing agent and on dispersibility of a carrier in the case of using the carrier. Further, a mixed solvent of these compounds and water can also be used.

When a gas is used as a reducing agent at the time of liquid-phase reduction, it is preferable to carry out the reduction in a pressure device such as autoclave in order to increase the solubility of the gas into a solution of the noble metal. At this time, it is preferable to pressurize inside the pressure device by the reducing agent. The pressure is preferably 0.1 MPa or more and preferably 1.0 MPa or less.

When the reducing agent is a liquid, a device for carrying out reduction of the noble metal compound or an oxidized noble metal is not particularly limited and the reduction can be carried out by adding a reducing agent into a solution of the noble metal. The quantity of the reducing agent to be used is not particularly limited, however, it is preferably 1 mole or more and preferably 100 moles or less to 1 mole of the noble metal atom.

The reduction temperature and the reduction time are variable depending on the reducing agent, however, the reduction temperature is preferably −5° C. or higher and more preferably 15° C. or higher, and preferably 150° C. or lower and more preferably 80° C. or lower. The reduction time is preferably 0.1 hour or more, more preferably 0.25 hour or more, and furthermore preferably 0.5 hour or more, and preferably 4 hours or less, more preferably 3 hours or less, and furthermore preferably 2 hours or less.

The catalyst is separated after the reduction. The method for separating the catalyst is not particularly limited, and for example, a filtration method or a centrifugation method can be used. The existence of the noble metal in a solvent thus separated can be easily confirmed by adding a reducing agent such as hydrazine. The quantity of the noble metal in the solvent can be quantitatively determined by elemental analysis such as ICP. It is preferable to carry out washing treatment of a thus separated catalyst by water or a solvent to be used in the reaction. The method for washing is not particularly limited and various methods can be used. The separated and washed catalyst is properly dried. The method for drying is not particularly limited and various methods can be used.

Examples

Hereinafter, the present invention will be more concretely explained by examples and comparative examples, however, the present invention is not limited to these Examples. The analysis of raw materials and products in the following examples and comparative examples was carried out using gas chromatography. Now, selectivities to an olefin, an α,β-unsaturated aldehyde, and α,β-unsaturated carboxylic acid, respectively, are defined as follows.

Selectivity to an olefin (%)=$(B/A) \times 100$

Selectivity to an α,β-unsaturated aldehyde (%)=$(C/A) \times 100$

Selectivity to an α,β-unsaturated carboxylic acid (%)=$(D/A) \times 100$

In the above formulae, A represents a number of moles of an alcohol reacted, B represents a number of moles of an olefin produced, C represents a number of moles of an α,β-unsaturated aldehyde produced, and D represents a number of moles of an α,β-unsaturated carboxylic acid produced. In the following examples and comparative examples, dehydration and oxidation of t-butanol are carried out, so that produced components are isobutylene, methacrolein, and methacrylic acid. In the following examples (except Example 5) and comparative examples, t-butanol which is a raw material is also used as a reaction solvent, it is difficult to measure the number of moles of t-butanol reacted, i.e. A. Therefore, numbers of moles of produced isobutylene, methacrolein, methacrylic acid, and other by-products, i.e. acetone, acetic acid, acrolein, acrylic acid, methacrylic acid anhydride, carbon monoxide, and carbon dioxide, are measured and the sum of them was regarded as the number of moles of t-butanol reacted, i.e. A, wherein in the case of a compound having other than 4 carbon atoms, this number of moles is converted into the number of moles of t-butanol having 4 carbon atoms; for example, in the case of acetic acid having 2 carbon atoms, the conversion is carried out by multiplying the number of moles of acetic acid by 2/4.

Example 1

(Preparation of Catalyst)

To 60 g of acetic acid, 1.1 g of palladium acetate was added, heated to 80° C., and dissolved to prepare a palladium acetic acid solution. To the acetic acid solution thus obtained, 10 g of zirconia powder having a specific surface area of 24 m²/g, an average particle diameter of 1 μm, and an $H_0$ greater than +4.8 was added as a carrier and the resultant mixture was evaporated. Subsequently the thus obtained matter was heated from room temperature to 450° C. at a rate of 2.5° C./minute in air, held at 450° C. for 3 hours as a heat treatment, and after that, it was cooled to room temperature. To the powder thus subjected to heat treatment, 50 g of 37% by mass aqueous formaldehyde solution was added. The resultant mixture was heated to 70° C., held at the same temperature for 2 hours while stirred, filtrated under suction, and the obtained solid matter was filtrated while washed with 1,000 g of pure water. Further, the resultant solid matter was dried at 100° C. for 2 hours under a nitrogen flow to obtain 10.5 g of a zirconia-supported palladium-containing catalyst having the palladium metal-loading ratio of 5.0% by mass.

(Evaluation of Reaction)

To an autoclave equipped with a gas inlet port (hereinafter, referred to as a reactor), 100 g of 75% by mass aqueous t-butanol solution, 10.5 g of the above-mentioned prepared catalyst, and 200 ppm of p-methoxyphenol based on the reaction solvent as a radical trapping agent were added, and the reactor was shut tight.

Subsequently, stirring of the resultant mixture was started at 1,000 rpm and the temperature of the mixture was raised to 130° C. After the raising of the temperature was completed, nitrogen was introduced into the reactor to the internal pressure of 2.4 MPa and then compressed air was introduced into the reactor to the internal pressure of 4.8 MPa and the reaction was started. At this time, about 35 mmol of oxygen was introduced. Drop of the internal pressure was observed with the progress of the reaction, and when the internal pressure dropped by 0.1 MPa, pure oxygen was added to the reactor to the internal pressure of 4.8 MPa (about 65 mmol). The sum of the added pure oxygen was 0.9 MPa. The stirring was continued in this state for 60 minutes and the reaction was finished.

After the reaction was finished, the liquid inside the reactor was cooled to 10° C. in an ice bath. A gas-sampling bag was attached to the gas outlet of the reactor and the gas outlet was opened to recover all the gas components. From the reactor, 1 g of the reaction liquid was sampled and separated into the catalyst and the reaction liquid using a membrane filter having a pore size of 0.5 μm. Each component contained in the recovered reaction liquid and gas was quantitatively analyzed with gas chromatography. The evaluation results are shown in Table 1.

Example 2

(Preparation of Catalyst)

The same procedure as in Example 1 was carried out except that silica powder having a specific surface area of 528 m$^2$/g, an average particle diameter of 58 μm, and an $H_0$ greater than +3.3 and not greater than +4.0, which is an acidic substance, was used as a carrier. Consequently, 10.5 g of a silica-supported palladium-containing catalyst having the palladium metal-loading ratio of 5.0% by mass was obtained.

(Evaluation of Reaction)

The same procedure as in Example 1 was carried out except that 10.5 g of the above-mentioned catalyst was used and evaluation of the reaction was carried out. The sum of the added pure oxygen was 1.6 MPa (about 115 mmol). The results are shown in Table 1.

Comparative Example 1

(Evaluation of Reaction)

The same procedure as in Example 1 was carried out except that 10.0 g of silica powder having a specific surface area of 528 m$^2$/g, an average particle diameter of 58 μm, and an $H_0$ greater than +3.3 and not greater than +4.0, on which palladium is not supported, was used and evaluation of the reaction was carried out. The reaction was not advanced, so that pure oxygen was not added. The results are shown in Table 1.

Example 3

(Preparation of Catalyst)

The same procedure as in Example 1 was carried out except that HY type zeolite having a $SiO_2/Al_2O_3$ molar ratio of 110, a specific surface area of 736 m$^2$/g, an average particle diameter of 3.3 μm, and an $H_0$ greater than −8.2 and not greater than −5.6, which is an acidic substance, was used as a carrier. Consequently, 10.5 g of HY type zeolite-supported palladium-containing catalyst having the palladium metal-loading ratio of 5.0% by mass was obtained.

(Evaluation of Reaction)

The same procedure as in Example 1 was carried out except that 10.5 g of the above-mentioned catalyst was used and the reaction temperature was set to 90° C. and evaluation of the reaction was carried out. The sum of the added pure oxygen was 0.8 MPa (about 58 mmol). The results are shown in Table 1.

Example 4

(Preparation of Catalyst)

The same procedure as in Example 1 was carried out except that HY type zeolite having a $SiO_2/Al_2O_3$ molar ratio of 70, a specific surface area of 757 m$^2$/g, an average particle diameter of 2.8 μm, and an $H_0$ greater than −8.2 and not greater than −5.6, which is an acidic substance, was used as a carrier. Consequently, 10.5 g of HY type zeolite-supported palladium-containing catalyst having the palladium metal-loading ratio of 5.0% by mass was obtained.

(Evaluation of Reaction)

The same procedure as in Example 1 was carried out except that 10.5 g of the above-mentioned catalyst was used and the reaction was finished at 50 minutes from the start and evaluation of the reaction was carried out. The sum of the added pure oxygen was 0.8 MPa (about 58 mmol). The results are shown in Table 1.

Example 5

(Preparation of Catalyst)

To 60 g of 88% by mass aqueous acetic acid solution, 1.1 g of palladium acetate was added, heated to 80° C., and dissolved. The resultant solution and 5.0 g of activated carbon powder having a specific surface area of 780 m$^2$/g and an average particle diameter of 30 μm were jointly charged in an autoclave and the autoclave was shut tight. Stirring of the resultant mixture was started at 500 rpm and the inside of the reaction system was substituted by nitrogen. Subsequently, the liquid inside the reactor was cooled to 10° C. or below, and propylene was introduced into the reactor to the internal pressure of 0.5 MPa, and the reaction system was held at 70° C. for 1 hour. After the lapse of 1 hour, the temperature of the liquid inside the reactor was cooled to 20° C. or below and the internal pressure was released. The slurry thus obtained was filtrated under suction under a nitrogen flow and the obtained solid matter was filtrated while washed with 1,000 g of pure water. Further, the resultant solid matter was dried at 100° C. for 2 hours under a nitrogen flow to obtain 5.5 g of an activated carbon-supported palladium-containing catalyst having the palladium metal-loading ratio of 10% by mass.

(Evaluation of Reaction)

Into the reactor, 100 g of 75% by mass aqueous acetone solution, 6 g of t-butanol, 3 g of dried Amberlyst-15 (trade name, strongly acidic ion exchange resin manufactured by Organo Corporation, functional group: —SO$_3$H, $H_0$ being not more than −8.2), 5.5 g of the above-mentioned prepared catalyst, and 200 ppm of p-methoxyphenol based on the reaction solvent as a radical trapping agent were added, and the reactor was shut tight. Subsequently, the same procedure as in Example 1 was carried out except that the reaction temperature was set to 90° C. and the reaction was finished in 50 minutes from the start. The sum of the added pure oxygen was 0.6 MPa (about 43 mmol). The results are shown in Table 1.

Example 6

(Evaluation of Reaction)

The same procedure as in Example 5 was carried out except that 100 g of 75% by mass aqueous acetone solution and 6 g of t-butanol, all of which were used in Example 5, were changed to 100 g of 75% by mass aqueous t-butanol solution and evaluation of the reaction was carried out. The sum of the added pure oxygen was 1.4 MPa (about 100 mmol). The results are shown in Table 1.

Comparative Example 2

(Evaluation of Reaction)

The same procedure as in Example 6 was carried out except that dried Amberlyst-15 (trade name, manufactured by Organo Corporation) was not used and evaluation of the reaction was carried out. The reaction was not advanced, so that pure oxygen was not added. The results are shown in Table 1.

TABLE 1

| | Reaction temperature (° C.) | Acidic substance [H₀] | Catalyst/Carrier | Reaction solvent | Selectivity to isobutylene (%) | Selectivity to methacrolein (%) | Selectivity to methacrylic acid (%) |
|---|---|---|---|---|---|---|---|
| Example 1 | 130 | None | Pd/Zirconia | 75% aqueous t-butanol solution | 31.9 | 33.7 | 8.4 |
| Example 2 | 130 | Silica (Catalyst Carrier) [+3.3 < H₀ ≦ +4.0] | Pd/Silica | 75% aqueous t-butanol solution | 33.1 | 19.8 | 17.8 |
| Example 3 | 90 | HY type zeolite (Catalyst Carrier) [−8.2 < H₀ ≦ −5.6] | Pd/HY type zeolite | 75% aqueous t-butanol solution | 49.8 | 26.5 | 13.8 |
| Example 4 | 90 | HY type zeolite (Catalyst Carrier) [−8.2 < H₀ ≦ −5.6] | Pd/HY type zeolite | 75% aqueous t-butanol solution | 55.2 | 28 | 8.1 |
| Example 5 | 90 | Amberlyst-15 (trade name) [H₀ ≦ −8.2] | Pd/Activated carbon | 75% aqueous acetone solution | 21.8 | 30.4 | 19.3 |
| Example 6 | 90 | Amberlyst-15 (trade name) [H₀ ≦ −8.2] | Pd/Activated carbon | 75% aqueous t-butanol solution | 63.5 | 19 | 9.6 |
| Comp. Ex. 1 | 130 | Silica [+3.3 < H₀ ≦ +4.0] | None | 75% aqueous t-butanol solution | 0 | 0 | 0 |
| Comp. Ex. 2 | 90 | none | Pd/Activated carbon | 75% aqueous t-butanol solution | 0 | 0 | 0 |

What is claimed is:

1. A method, which comprises
dehydrating and oxidizing an alcohol in a liquid phase, in one vessel, in the presence of molecular oxygen and a noble metal-comprising catalyst at a temperature in the range of 110 to 250° C., thereby obtaining at least one of an α,β-unsaturated aldehyde and an α,β-unsaturated carboxylic acid from the alcohol.

2. A method, which comprises
dehydrating and oxidizing an alcohol in a liquid phase, in one vessel, in the presence of molecular oxygen, a noble metal-comprising catalyst, and an acidic substance having a $H_0$, a Hammett Acidity Function, of not higher than +4.8, thereby obtaining at least one of an α,β-unsaturated aldehyde and an α,β-unsaturated carboxylic acid from the alcohol.

3. The method according to claim 1, wherein said dehydrating and oxidizing are carried out simultaneously.

4. The method according to claim 2, wherein said dehydrating and oxidizing are carried out simultaneously.

5. The method according to claim 1, wherein said alcohol is at least one member selected from the group consisting of isopropanol, t-butanol, and n-butanol.

6. The method according to claim 2, wherein said alcohol is at least one member selected from the group consisting of isopropanol, t-butanol, and n-butanol.

7. The method according to claim 1, wherein said alcohol is t-butanol.

8. The method according to claim 2, wherein said alcohol is t-butanol.

9. The method according to claim 1, wherein said noble metal-comprising catalyst comprises at least one noble metal selected from the group consisting of palladium, platinum, rhodium, ruthenium, iridium, gold, silver, and osmium.

10. The method according to claim 2, wherein said noble metal-comprising catalyst comprises at least one noble metal selected from the group consisting of palladium, platinum, rhodium, ruthenium, iridium, gold, silver, and osmium.

11. The method according to claim 1, wherein said noble metal-comprising catalyst comprises at least one noble metal selected from the group consisting of palladium, platinum, rhodium, ruthenium, iridium, gold, silver, and osmium, where the at least one noble metal is present in the noble metal-comprising catalyst in an amount of at least 50% by mass.

12. The method according to claim 2, wherein said noble metal-comprising catalyst comprises at least one noble metal selected from the group consisting of palladium, platinum, rhodium, ruthenium, iridium, gold, silver, and osmium, where the at least one noble metal is present in the noble metal-comprising catalyst in an amount of at least 50% by mass.

13. The method according to claim 2, wherein said acidic substance is at least one member selected from the group consisting of a sulfuric acid, a phosphoric acid, phosphomolybdic acid, a salt of phosphomolybdic acid, phosphotungstic acid, a salt of phosphotungstic acid, silicomolybdic acid, a salt of silicomolybdic acid, silicotungstic acid, a salt of silicotungstic acid, silica, alumina, silica-alumina, γ-alumina, zirconia, and titania, a HY zeolite and mordenite, and an acidic ion-exchange resin.

14. The method according to claim 1, wherein said noble metal-comprising catalyst is present on a carrier that has a specific surface area of from 100 to 5,000 m²/g.

15. The method according to claim 2, wherein said noble metal-comprising catalyst is present on a carrier that has a specific surface area of from 100 to 5,000 m²/g.

16. The method according to claim 1, wherein said dehydrating and oxidizing are carried out a pressure of from 0 to 10 MPa.

17. The method according to claim 2, wherein said dehydrating and oxidizing are carried out a pressure of from 0 to 10 MPa.

18. The method according to claim 1, wherein said dehydrating and oxidizing are carried out a pressure of from 2 to 7 MPa.

19. The method according to claim 2, wherein said dehydrating and oxidizing are carried out a pressure of from 2 to 7 MPa.

20. The method according to claim 2, wherein said alcohol is t-butanol, said noble metal-comprising catalyst comprises palladium and is present on a silica support, said acidic substance comprises silica, and a product obtained by said dehydrating and oxidizing comprises methacrolein and methacrylic acid.

* * * * *